(12) United States Patent
Snell

(10) Patent No.: US 6,904,313 B1
(45) Date of Patent: Jun. 7, 2005

(54) METHODS AND SYSTEMS FOR MONITORING HEART RATE RECOVERY

(75) Inventor: Jeffery D. Snell, Chatsworth, CA (US)

(73) Assignee: Pacesetter, Inc., Sylmar, CA (US)

( * ) Notice: Subject to any disclaimer, the term of this patent is extended or adjusted under 35 U.S.C. 154(b) by 422 days.

(21) Appl. No.: 10/154,946

(22) Filed: May 23, 2002

(51) Int. Cl.[7] ............................................. A61B 5/04
(52) U.S. Cl. ..................................... 600/519; 607/509
(58) Field of Search .................. 600/509, 519–520; 607/4–5, 9, 13, 17, 19, 24

(56) References Cited

U.S. PATENT DOCUMENTS

| | | | |
|---|---|---|---|
| 4,898,182 A | | 2/1990 | Hawkins et al. ............ 600/520 |
| 5,836,988 A | * | 11/1998 | Cooper et al. ................ 607/19 |
| 5,931,858 A | * | 8/1999 | Kadhiresan et al. .......... 607/20 |
| 6,190,324 B1 | | 2/2001 | Kieval et al. ................ 600/483 |
| 6,459,934 B1 | | 10/2002 | Kadhiresan ..................... 607/9 |
| 6,768,919 B2 | * | 7/2004 | Starobin et al. ............ 600/520 |
| 2001/0037067 A1 | | 11/2001 | Tchou et al. ................ 600/483 |
| 2002/0198462 A1 | | 12/2002 | Begemann .................. 600/519 |
| 2003/0004424 A1 | * | 1/2003 | Birnbaum et al. .......... 600/520 |

FOREIGN PATENT DOCUMENTS

| | | | | |
|---|---|---|---|---|
| EP | 0 580 128 A2 | * | 7/1993 | ............ A61N/1/365 |
| WO | WO 98/56460 | * | 12/1998 | ............. A61N/1/39 |

OTHER PUBLICATIONS

Cole et al, "Heart–Rate Recovery Immediately after Exercise as a Predictor of Mortality", Oct. 28, 1999, The New England Medical Journal or Medicine, vol. 341(18). pp. 1351–1357.*

* cited by examiner

*Primary Examiner*—Carl Layno

(57) ABSTRACT

Methods and systems for monitoring heart rate recovery are described. In one embodiment, an implantable monitoring device monitors a patient's heart activity. The monitor looks for periods of increased activity, such as those that are experienced during some level of exercise, and periods of lesser activity (such as rest) directly following. The patient's heart rate recovery is monitored as the heart recovers from the active period to the rest period. Data associated with the patient's heart rate recovery can then be diagnostically used to ascertain certain conditions associated with the patient.

27 Claims, 7 Drawing Sheets

METHODS AND SYSTEMS FOR MONITORING HEART RATE RECOVERY

TECHNICAL FIELD

The present invention generally relates to implantable monitoring devices, such as implantable stimulation devices and the like.

BACKGROUND

The human heart is an extremely complex organ and has many operational parameters that can be useful to study in order to gain an appreciation for the heart's operation. Certain parameters can be used to not only assess the health and operation of the heart, but can be a powerful predictive tool for predicting certain aspects pertaining to the owner of the heart. Not surprisingly, ongoing medical and clinical research seems to find new and different correlations between heart parameters and information that is of interest to physicians. As these parameters and correlations are discovered, it would be highly desirable to make use of them in an integrated and convenient fashion.

As an example, consider the following. Many times the parameters and correlations mentioned above are such that they can only conveniently be studied and observed in a clinical setting, i.e. in the doctor's office. To observe the parameters and gather the information that is to be used to generate the desired correlations, the patient may be required to be connected to expensive medical testing devices. One image that comes to mind is the image of a heart patient, wired to a heart monitor, running or walking briskly on a treadmill in the doctor's office so that the doctor can gather information about how their heart performs under exercise conditions. While the information is useful to the doctor, it might be useful, in some instances, to gather the data in locations other than the doctor's office so that the desired correlations can be later (or contemporaneously) computed.

Accordingly, this invention arose out of concerns associated with providing methods and systems that enable heart parameters, useful in computing desired correlations, to be conveniently and flexibly collected and saved.

SUMMARY

Methods and systems for monitoring heart rate recovery are described. In one embodiment, an implantable monitoring device monitors a patient's heart activity. The monitor looks for periods of increased activity, such as those that are experienced during some level of exercise, and periods of lesser activity (such as rest) directly following. The patient's heart rate recovery is monitored as the heart recovers from the active period to the rest period. Data associated with the patient's heart rate recovery can then be diagnostically used to ascertain certain conditions associated with the patient.

BRIEF DESCRIPTION OF THE DRAWINGS

The following description is of the best mode presently contemplated for practicing the invention. This description is not to be taken in a limiting sense but is made merely for the purpose of describing the general principles of the invention. The scope of the invention should be ascertained with reference to the issued claims.

DETAILED DESCRIPTION

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Overview

Methods and systems for monitoring heart rate recovery are described. In one embodiment, an implantable monitoring device monitors a patient's heart activity. The monitor looks for periods of increased activity, such as those that are experienced during some level of exercise, and periods of lesser activity (such as rest) directly following. The patient's heart rate recovery is monitored as the heart recovers from the active period to the rest period. Data associated with the patient's heart rate recovery can be used to ascertain, in some instances probabilistically, certain conditions associated with the patient. For example, an overly fast heart rate recovery may suggest some problems that require further study. An overly slow heart rate recovery may suggest other problems that require further study.

Any suitable implantable heart monitor can be used. In certain embodiments, the heart monitor may, but need not, have other functions such as cardiac rhythm management functions.

Cardiac rhythm management devices (or stimulation devices as they are sometimes called), including implantable devices, can include, for example, implantable cardiac pacemakers, cardioverters or defibrillators. The devices are generally implanted in an upper portion of the chest, in either the left or right side depending on the type of the device, beneath the skin of a patient within what is known as a subcutaneous pocket. The implantable devices generally function in association with one or more electrode-carrying leads which are implanted within the heart. The electrodes are typically positioned within the right side of the heart, either the right ventricle or right atrium, or both, for making electrical contact with their designated heart chamber. Conductors within the leads couple the electrodes to the device to enable the device to deliver the desired stimulation therapy.

An exemplary device is described below in connection with FIGS. 1 and 2.

Exemplary Stimulation Device

The following description sets forth but one exemplary stimulation device that is capable of being used in connection with the various embodiments that are described below. It is to be appreciated and understood that other stimulation devices, including those that are not necessarily implantable, can be used and that the description below is given, in its specific context, to assist the reader in understanding, with more clarity, the inventive embodiments described herein.

Figure 1:
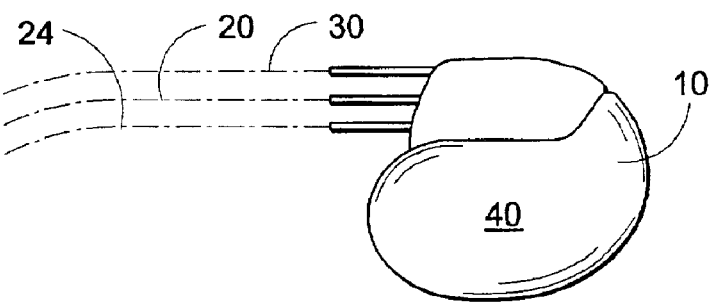
FIG. 1 is a simplified diagram illustrating an implantable stimulation device in electrical communication with at least three leads implanted into a patient's heart for delivering multi-chamber stimulation and shock therapy.
Figure 1:
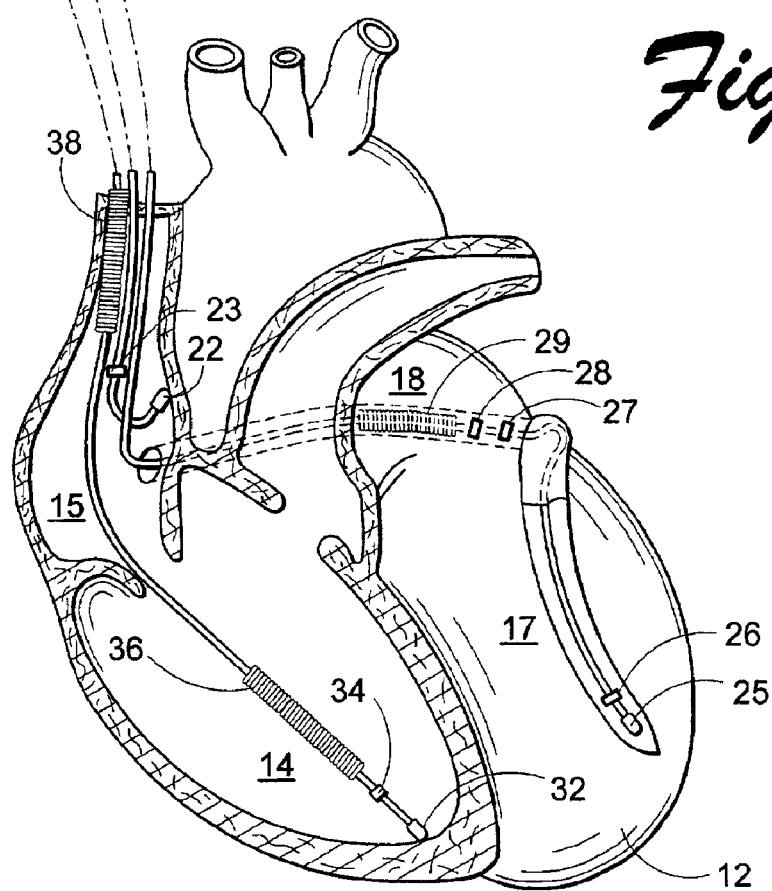

FIG. 1 illustrates a stimulation device 10 in electrical communication with a patient's heart 12 suitable for delivering multi-chamber stimulation and shock therapy. The portions of the heart 10 illustrated include the right ventricle 14, the right atrium 15, the left ventricle 17, and the left atrium 18. As used herein, the left-side of the heart is meant to denote the portions of the heart encompassing the left ventricle 17 and the left atrium 18 and those portions of the coronary sinus, great cardiac vein, and its associated tributaries, which are adjacent the left atrium and left ventricle. Device 10 is desirably configured to monitor heart rate recovery. This can be done using sensors that are onboard the device. Data associated with the heart rate recovery can then be stored for later use, such as transmission to a programmer for analysis.

To sense atrial cardiac signals and to provide right atrial chamber stimulation therapy, the stimulation device 10 is coupled to an implantable right atrial lead 20 having at least an atrial tip electrode 22, and preferably a right atrial ring electrode 23, which typically is implanted in the patient's right atrial appendage.

To sense left atrial and ventricular cardiac signals and to provide left-chamber pacing therapy, the stimulation device 10 is coupled to a "coronary sinus" lead 24 designed for placement in the "coronary sinus region" via the coronary sinus os so as to place one or more distal electrodes adjacent to the left ventricle 17 and one or more proximal electrodes adjacent to the left atrium 18. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, the coronary sinus lead 24 is designed to receive atrial and ventricular cardiac signals and to deliver: left ventricular pacing therapy using, for example, a left ventricular tip electrode 25 and a left ventricular ring electrode 26; left atrial pacing therapy using, for example, a first and second left atrial ring electrode, 27 and 28; and shocking therapy using at least a left atrial coil electrode 29.

The stimulation device 10 is also shown in electrical communication with the patient's heart 12 by way of an implantable right ventricular lead 30 having a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode 36 will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle 14.

Figure 2:
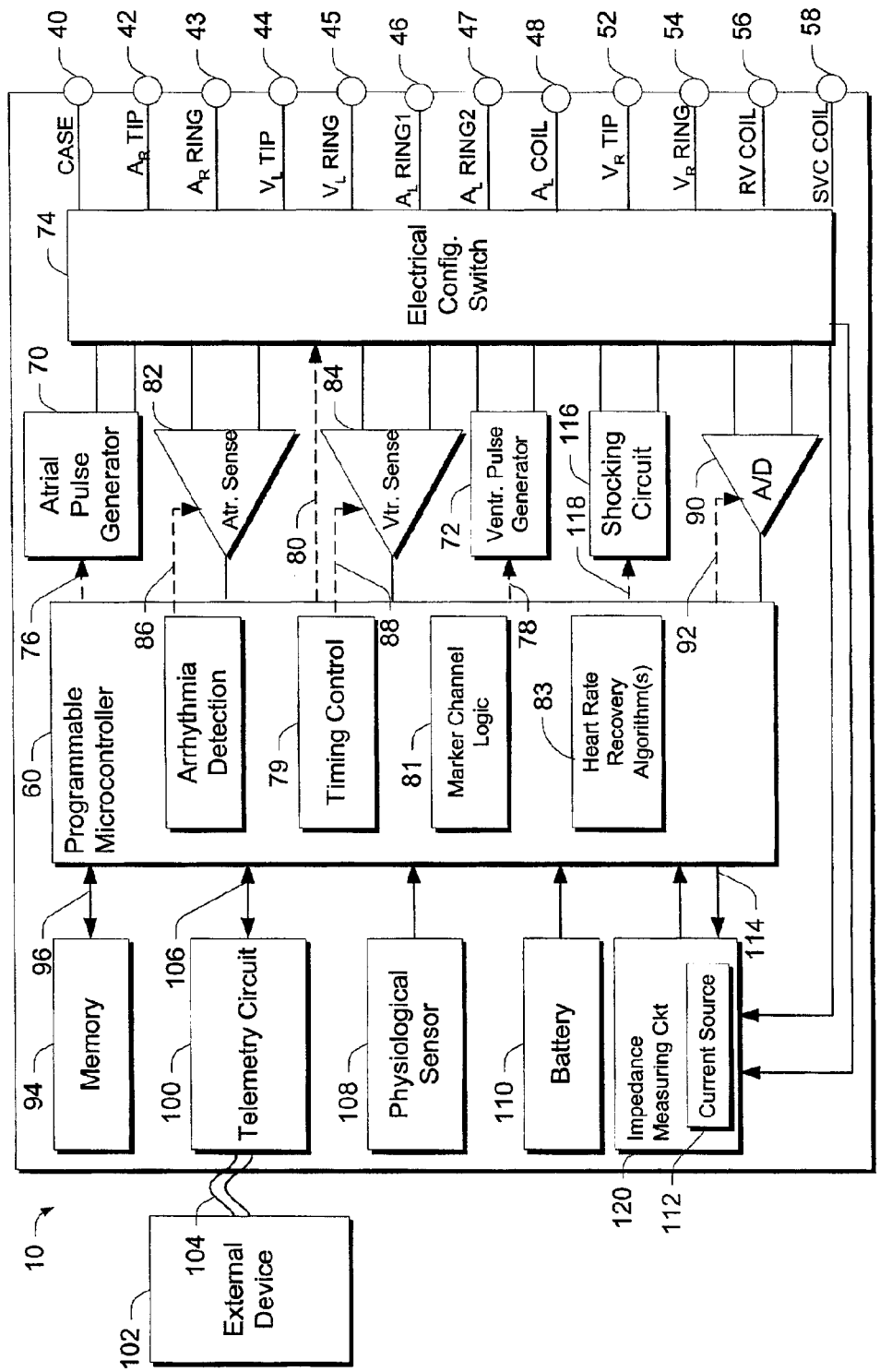
FIG. 2 is a functional block diagram of a multi-chamber implantable stimulation device illustrating exemplary basic elements of a stimulation device which can provide cardioversion, defibrillation and/or pacing stimulation in up to four chambers of the heart.

FIG. 2 illustrates a simplified block diagram of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and/or pacing stimulation. In addition, it will be appreciated and understood that various processing steps about to be described can be implemented in the form of software instructions that are resident on a computer-readable media that is located on the stimulation device. Accordingly, aspects of the invention described herein extend to all forms of computer-readable media, whether on the stimulation device (or monitoring device) or not, when such media contains instructions that, when executed by one or more processors, implement the methods described herein.

The stimulation device 10 includes a housing 40 which is often referred to as "can", "case" or "case electrode", and which may be programmably selected to act as the return electrode for all "unipolar" modes. The housing 40 may further be used as a return electrode alone or in combination with one or more of the coil electrodes 29, 36, or 38, for shocking purposes.

The housing 40 further includes a connector (not shown) having a plurality of terminals, 42, 43, 44, 45, 46, 47, 48, 52, 54, 56, and 58 (shown schematically and, for convenience, the names of the electrodes to which they are connected are shown next to the terminals). While it is recognized that current devices are limited to the number of terminals due to International Standards, one of skill in the art could readily eliminate some of the terminals/electrodes to fit in the existing device configurations and permit programmability to select which terminals connect to which electrodes. However, in the near future, the standards may change to permit multi-polar in-line connectors, and multiple feedthroughs connectors could readily be manufactured to accommodate the configuration shown in FIG. 2.

As such, to achieve right atrial sensing and pacing, the connector includes at least a right atrial tip terminal 42 and a right atrial ring terminal 43, adapted for connection to the atrial tip electrode and ring electrodes 22 and 23, respectively.

To achieve left chamber sensing, pacing and/or shocking, the connector includes at least a left ventricular tip terminal 44, a left ventricular ring electrode 45, a first left atrial ring terminal 46, a second left atrial ring terminal 47, and a left atrial shocking terminal 48, which are adapted for connection to the left ventricular tip electrode 25, left ventricular ring 26, the first left atrial tip electrode 27, the second left atrial ring electrode 28, and the left atrial coil electrode 29, respectively.

To support right chamber sensing, pacing and/or shocking, the connector further includes a right ventricular tip terminal 52, a right ventricular ring terminal 54, a right ventricular (RV) shocking terminal 56, and an SVC shocking terminal 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller or microprocessor 60 that controls the various modes of stimulation therapy. As is well known in the art, the microcontroller 60 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via a switch bank 74. It is understood that in order to provide stimulation therapy in each of the four chambers of the heart, the atrial pulse generator 70 and the ventricular pulse generator 72 may include dedicated, independent pulse generators, multiplexed pulse generators, or shared pulse generators. The atrial pulse generator 70 and the ventricular pulse generator 72 are controlled by the microcontroller 60 via appropriate control signals 76 and 78, respectively, to trigger or inhibit the stimulation pulses.

The microcontroller 60 further includes timing control circuitry 79 which is used to control the timing of such stimulation pulses (e.g., pacing rate, atrioventricular (AV) delay, atrial interconduction (A—A) delay, or ventricular interconduction (V—V) delay, etc.), as well as to keep track of the timing of refractory periods, PVARP intervals, noise detection windows, evoked response windows, alert intervals, marker channel timing (via marker channel logic 81), etc., which is well known in the art.

In one embodiment, the microcontroller can be programmed with one or more heart rate recovery algorithms 83. The heart rate recovery algorithm(s) operate to monitor a patient's heart rate recovery when, for example, the patient recovers from a period of exercise to a period of rest. The algorithms can then save data associated with the heart rate recovery for later (or contemporaneous) use.

The switch bank 74 includes a plurality of switches for connecting the desired electrodes to the appropriate I/O circuits, thereby providing complete electrode programmability. Accordingly, the switch bank 74, in response to a control signal 80 from the microcontroller 60, determines the polarity of the stimulation pulses (e.g. unipolar, bipolar, combipolar, etc.) and various shocking vectors by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch bank 74, for detecting the presence of cardiac activity in each of the four chambers of the heart. Accordingly, the atrial and ventricular sensing circuits 82 and 84 may include dedicated sense amplifiers, multiplexed amplifiers, or shared amplifiers. The switch bank 74 determines the "sensing polarity" of the cardiac signal by selectively closing the appropriate switches. In this way, the clinician may program the sensing polarity independent of the stimulation polarity.

The atrial sensing circuit 82 or the ventricular sensing circuit 84 preferably employ one or more low power, precision amplifiers with programmable gain and/or automatic gain control, bandpass filtering, and a threshold detection circuit, to selectively sense the cardiac signal of interest. The automatic gain control enables the stimulation device 10 to deal effectively with the difficult problem of sensing the low amplitude signal characteristics of atrial or ventricular fibrillation. The outputs of the atrial and ventricular sensing circuits, 82 and 84, are connected to the microcontroller 60 for triggering or inhibiting the atrial and ventricular pulse generators, 70 and 72, respectively, in a demand fashion, in response to the absence or presence of cardiac activity, respectively, in the appropriate chambers of the heart.

For arrhythmia detection, the stimulation device 10 utilizes the atrial and ventricular sensing circuits, 82 and 84, to sense cardiac signals for determining whether a rhythm is physiologic or pathologic. As used herein "sensing" is reserved for the noting of an electrical signal, and "detection" is the processing of these sensed signals and noting the presence of an arrhythmia. The timing intervals between sensed events (e.g. P-waves, R-waves, and depolarization signals associated with fibrillation which are sometimes referred to as "F-waves" or "Fib-waves") are then classified by the microcontroller 60 by comparing them to a predefined rate zone limit (e.g. bradycardia, normal, low rate VT, high rate VT, and fibrillation rate zones) and various other characteristics (e.g. sudden onset, stability, physiologic sensors, and morphology, etc.) in order to determine the type of remedial therapy that is needed (e.g. bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into digital signals, and store the digital signals for later processing and/or telemetric transmission to an external device 102. The data acquisition system 90 is coupled to the right atrial lead 20, the coronary sinus lead 24, and the right ventricular lead 30 through the switch bank 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the stimulation device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller 60 by a control signal 106. The telemetry circuit 100 advantageously allows intracardiac electrograms and status information relating to the operation of the stimulation device 10 (as contained in the microcontroller 60 or memory 94) to be sent to the external device 102 through the established communication link 104.

The stimulation device 10 can further include one or more physiologic sensors 108. Some physiologic sensors are referred to as a "rate-responsive" sensors because they are typically used to adjust pacing stimulation rate according to the exercise state of the patient. However, physiological sensors 108 may further be used to detect changes in cardiac output, changes in the physiological condition of the heart, patient activity, or diurnal changes in activity (e.g. detecting sleep and wake states). A physiological parameter of the heart, which may be measured to optimize such pacing and to indicate when such pacing may be inhibited or terminated is the stroke volume of the heart. Accordingly, the microcontroller 60 responds by adjusting the various pacing parameters (such as rate, AV Delay, A—A Delay, V—V Delay, etc.) at which the atrial and ventricular pulse generators, 70 and 72, generate stimulation pulses. A common type of rate responsive sensor is an activity sensor, such as an accelerometer or a piezoelectric crystal, which is mounted within the housing 40 of the stimulation device 10. Other types of physiologic sensors are also known, for example, sensors which sense the oxygen content of blood, respiration rate and/or minute ventilation, pH of blood, ventricular gradient, etc.

The stimulation device 10 additionally includes a power source such as a battery 110 that provides operating power to all the circuits shown in FIG. 2. For the stimulation device 10, which employs shocking therapy, the battery 110 is capable of operating at low current drains for long periods of time, and also be capable of providing high-current pulses (for capacitor charging) when the patient requires a shock pulse. The battery 110 preferably has a predictable discharge characteristic so that elective replacement time can be detected. Accordingly, the stimulation device 10 can employ lithium/silver vanadium oxide batteries.

It can be a primary function of the stimulation device 10 to operate as an implantable cardioverter/defibrillator (ICD) device. That is, it can detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5–10 joules), or high (11 to 40 joules) energy, as controlled by the microcontroller 60. Such shocking pulses are applied to the patient's heart through at least two shocking electrodes, and as shown in this embodiment, selected from the left atrial coil electrode 29, the RV coil electrode 36, and/or the SVC coil electrode 38 (FIG. 1). As noted above, the housing 40 may act as an active electrode in combination with the RV electrode 36, or as part of a split electrical vector using the SVC coil electrode 38 or the left atrial coil electrode 29 (i.e., using the RV electrode as the common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

As further shown in FIG. 2, the stimulation device 10 can have an impedance measuring circuit 120 including an impedance measuring current source 112 and a voltage measuring circuit 90 (shown in FIG. 2 as an A/D converter), which can be enabled by the microcontroller 60 by a control signal 114 for providing stroke volume measurements of the heart. The current source 112 can provide an alternating or pulsed excitation current. The voltage measuring circuitry 90 may also take the form of, for example, a differential amplifier.

The uses for an impedance measuring circuit 120 include, but are not limited to, lead impedance surveillance during the acute and chronic phases for proper lead positioning or dislodgment; detecting operable electrodes and automatically switching to an operable pair if dislodgment occurs; measuring a respiration parameter (for example, tidal volume, respiration rate, minute ventilation or volume, abnormal or periodic breathing); measuring thoracic impedance for determining shock thresholds and shock timing (corresponding to the diastolic time); detecting when the device has been implanted; measuring a cardiac parameter (such as, stroke volume, wall thickness, left ventricular volume, etc.); and detecting the opening of the valves, etc. In the present embodiment, the impedance measuring circuit is used to monitor left heart disease and provides appropriate stimulation therapy, such as altering rate, AV, A—A, or V—V delays. The impedance measuring circuit 120 can be advantageously coupled to the switch bank 74 so that any desired electrode can be used. Impedance may also be useful in verifying hemodynamic collapse to confirm that ATP has failed and/or VF has begun.

The microcontroller 60 is coupled to the voltage measuring circuit 90 and the current source 112 for receiving a magnitude of the established current and a magnitude of the monitored voltage. The microcontroller 60, operating under program instructions, divides the magnitude of the monitored or measured voltage by the magnitude of the established current to determine an impedance value. Once the impedance signals are determined, they may be delivered to the memory 94 for storage and later retrieved by the microcontroller 60 for therapy adjustment or telemetry transmission. The telemetry circuitry receives the impedance values from the microcontroller 60 and transmits them to the external programmer. The impedance value may then be monitored by the patient's physician to enable the physician to track the patient's condition.

The impedance measuring circuit 120 is advantageously coupled to the switch bank 74 so that any desired electrode may be used. The current source 112 may be programmably configured between a desired pair of electrodes, and the voltage measuring circuit 90 may be programmably configured between the same or preferably a different pair of electrodes.

Heart Rate Recovery Monitoring

Figure 3:
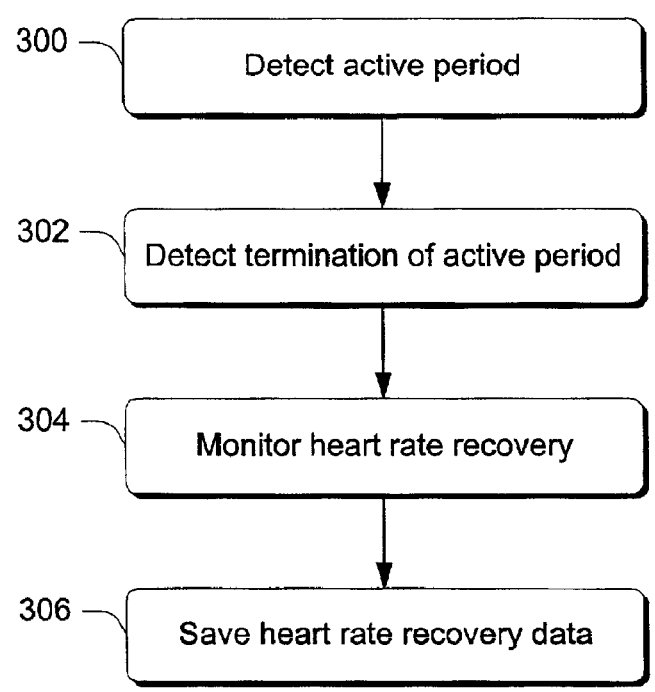
FIG. 3 is a flow diagram describing steps in a method in accordance with one embodiment.

FIG. 3 is a flow diagram that describes steps in a method in accordance with one embodiment. The steps can be implemented in any suitable hardware, software, firmware, or combination thereof. In the illustrated example, the steps can be implemented by a suitably programmed implantable heart monitoring device, such as a stimulation device that is similar to, or different from those described above.

Step 300 detects an active period. This step can be implemented using one or more physiologic sensors, such as those described above. For example, an activity sensor, such as an accelerometer or piezoelectric sensor, can detect when a patient is active. Exemplary techniques for determining patient activity are described in U.S. Pat. No. 6,128,534, the disclosure of which is incorporated by reference. These and other techniques can be used in accordance with the described embodiments. An active period can correspond to when a patient is exercising or otherwise exerting themselves in some manner. Exemplary exertions can include, for some patients, climbing the stairs, walking for a duration of time, working in the garden and the like. These active periods are characterized by an increase in the patient's heart rate. Step 302 detects termination of the active period. This step can be implemented utilizing the same physiologic sensor(s) utilized above. Step 304 monitors the patient's heart rate recovery as the patient's heart rate recovers from a generally elevated rate associated with the active period, to a rate more associated with a rest or inactive period. This step can be implemented using sensors that are typically utilized to monitor a patient's heart rate. Exemplary sensors are described above in connection with FIGS. 1 and 2. Step 306 can then save heart rate recovery data that is associated with the patient's heart rate recovery. This step can be implemented by saving the data in a memory onboard the monitoring device. Where the monitoring device comprises a stimulation device such as the one described above, the associated data can be stored in a memory such as memory 94.

The data, once collected by the monitoring device, can be further processed onboard the monitoring device, if the monitoring device is so equipped. Alternately, the monitoring device can simply save the data so that it can later provide the data to an external device for further processing.

Figure 4:
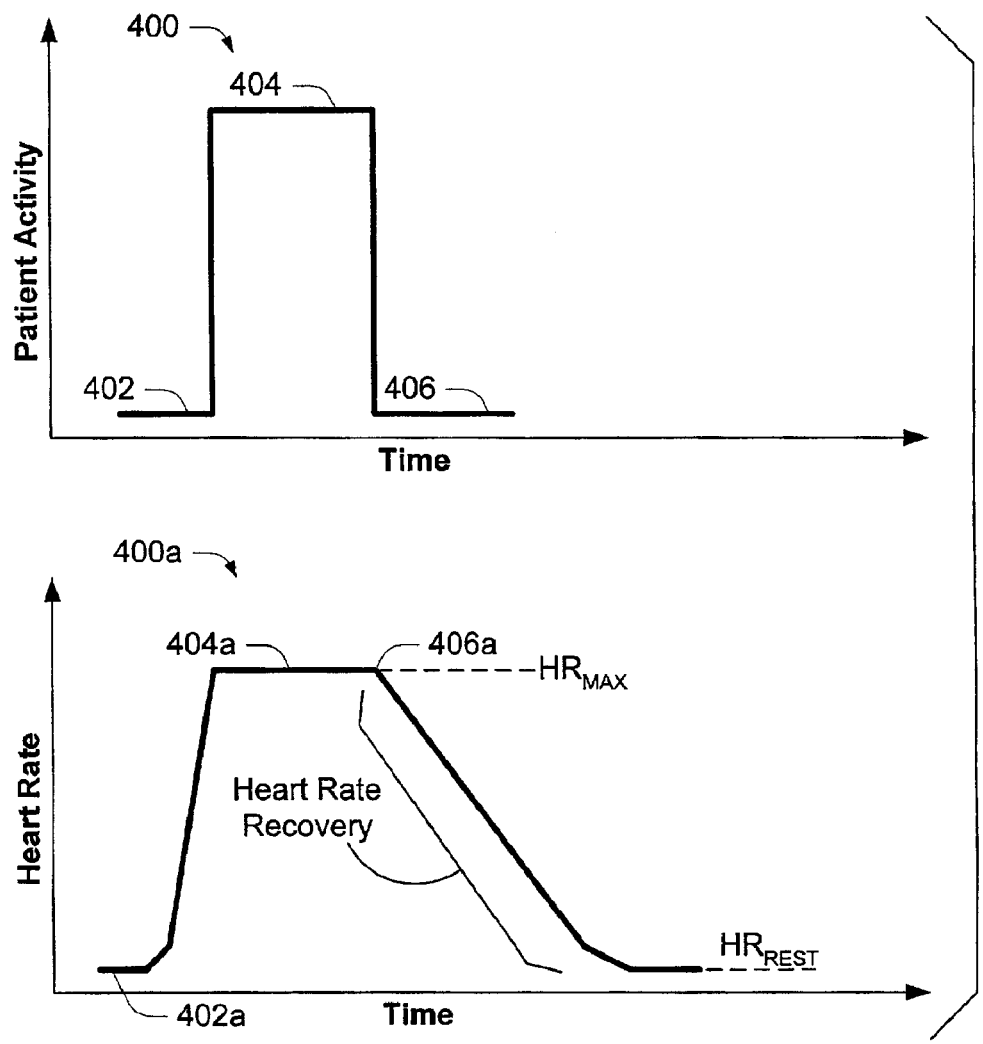
FIG. 4 is a diagram that depicts two graphs that are useful in understanding certain principles associated with the described embodiments.

FIG. 4 shows two graphs that are useful for understanding the processing that was just described. The graphs are particularly useful for visualizing what is meant by a heart rate recovery and how and when the heart rate recovery is monitored.

A first graph 400 plots patient activity versus time. In the graph, there is a period of general inactivity 402 followed by a period of activity 404 which, in turn, is followed by a period of general inactivity 406. For example, during period 402 the patient may be resting or nominally moving about. During period 404, perhaps the patient goes for a long vigorous walk or rides a bicycle. Period 406 coincides with the termination of the patient's exercise and a corresponding inactive period.

A second graph 400a plots a patient's heart rate versus time. This graph corresponds in time with first graph 400. Notice that during a period 402a, the patient's heart rate is at a first level that is associated with the inactive period 402. When the patient begins to exert themselves (corresponding to period 404), their heart rate begins to climb until it reaches a level designated as "$HR_{MAX}$" for a period 404a. When the patient terminates their activity or exertion, a period 406a begins during which the patient's heart rate recovers to its resting or inactive rate—designated as "$HR_{REST}$". It is the heart rate recovery between the termination of the exertion and the return to a lower, inactive heart rate that is monitored by the heart monitor.

Figure 5:
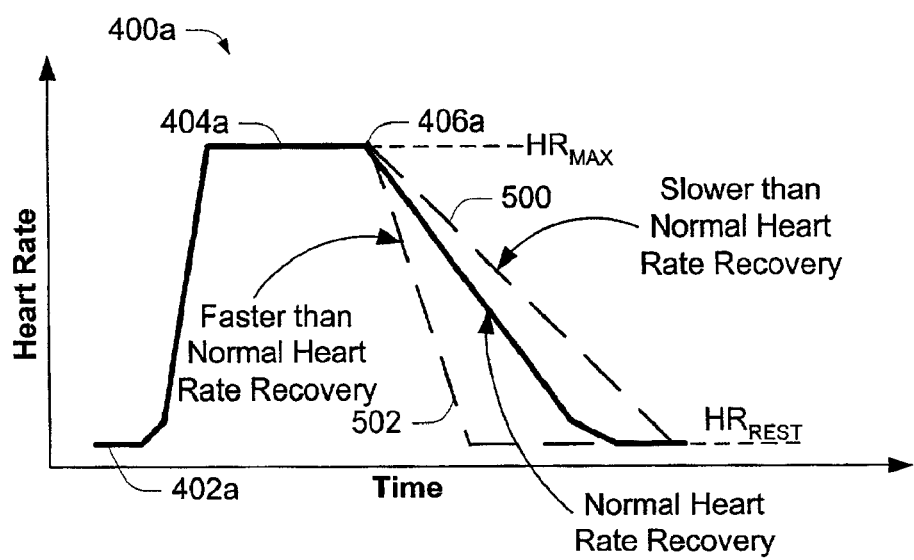
FIG. 5 is a graph that depicts a graph that is useful in understanding certain principles associated with the described embodiments.

Assume for purposes of discussion that the depicted heart rate recovery can be considered as a "normal" heart rate recovery. The term "normal" as it pertains to the patient's heart rate recovery can mean a couple of different things. A normal heart rate recovery can be one that is associated with a large group of individuals-perhaps across a cross section of people. So, in this case, a normal heart rate recovery might be one that is, on average, found to exist in a large group of individuals. One study, mentioned below, found a decrease of around 42 beats per minute to be about normal. Alternately, a normal heart rate recovery can be patient-specific. That is, there may be something about the patient that causes them to have a normal heart rate recovery that does not fit within what might be considered normal for a larger cross-section of individuals. Perhaps the patient is young or ailing FIG. 5 shows graph 400a along with two plots of heart rate recoveries that are outside of or trend away from what might be considered as "normal". Specifically, a first heart rate recovery plot 500 and a second heart rate recovery plot 502 are shown. The first heart rate recovery plot depicts a slower than normal heart rate recovery and the second heart rate recovery plot depicts a faster than normal heart rate recovery. Over time, an individual may exhibit a heart rate recovery that trends away from what can be considered as normal for that individual. The fact that a patient's heart rate recovery trends away from a normal heart rate recovery can be indicative of a problem or situation that might warrant further investigation. That is, the heart rate recovery of a patient can provide a diagnostic tool that can assist a doctor in assessing the health and viability of the patient. As an example, a patient may recently have had a change in medication which inadvertently affects their heart rate recovery. Knowing this can help the doctor assess whether a remedial action is necessary, e.g. changing the medication or lowering the dosage. A patient may have had a change in their electrolyte balance which, in turn, affects their heart rate recovery. Knowing this can assist the doctor in taking action to re-establish a normal electrolyte balance.

Monitoring heart rate recoveries can also assist, in stimulation device embodiments, with the administration of therapy and/or with further assessment of the patient for problems of which an abnormal heart rate recovery is symptomatic. Specifically, if the patient's heart rate recovery is faster than normal (corresponding to plot 502), then effectively their heart rate is more precipitously returning to normal than is desirable. This could lead to dizziness and possible loss of consciousness. By monitoring the heart rate recovery and ascertaining a trend away from normal and towards a faster heart rate recovery, the stimulation device can be programmed to administer pacing pulses to pace the patient back up to a more normal heart rate recovery. Conversely, having a heart rate recovery that is slower than normal (corresponding to plot 500) might be indicative of a condition that warrants further investigation. For example, if the patient is exercising, stops exercising and their heart rate remains high, this might be indicative of a tachyarrithmia which can then be further assessed and treated if necessary.

Additionally, heart rate recoveries can be a predictor of mortality. That is, studies have been done, most notably at the Cleveland Clinic, that have found a correlation between having an abnormal heart rate recovery and an increased likelihood of mortality. Specifically, in the study (published in the Apr. 4, 2000 issue of the Annals of Internal Medicine), over a 12 year period of time, only four percent of the patients with a normal heart rate recovery died, whereas ten percent of those with an abnormal heart rate recovery died. Accordingly, an abnormal heart rate recovery was associated with a 2½-fold increased risk of death.

Accordingly, having information that indicates a trend away from a normal heart rate recovery can assist a physician in diagnosing potential problems and suggesting remedial measures for a patient (e.g. diet changes, lifestyle changes, medication changes, and the like) that might increase the patient's life expectancy.

Figure 6:
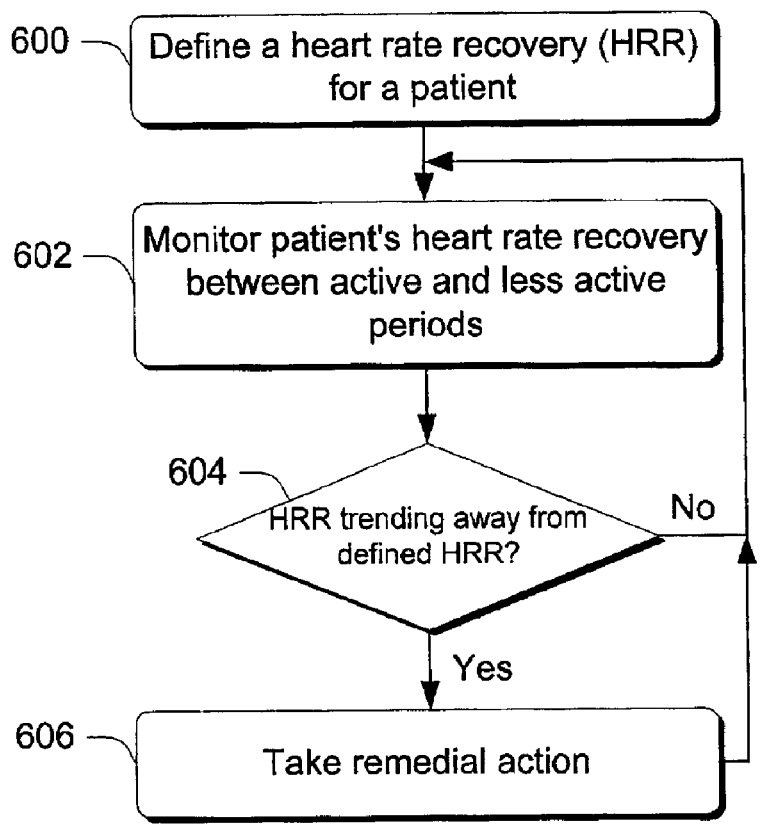
FIG. 6 is a flow diagram describing steps in a method in accordance with one embodiment.

FIG. 6 is a flow diagram that describes steps in a method in accordance with one embodiment. The steps can be implemented in any suitable hardware, software, firmware, or combination thereof. In the illustrated example, the steps can be implemented by a suitably programmed implantable heart monitoring device, such as a stimulation device that is similar to, or different from those described above.

Step 600 defines a normal heart rate recovery for a patient. This step can be implemented in a number of different ways. For example, a standardized heart rate recovery can be defined and programmed into a monitoring or stimulation device by, for example, the physician. Alternately, the heart rate recovery can be defined over time, by observing and monitoring the patient's heart rate recovery. For example, the monitoring or stimulation device can monitor the patient's heart rate recoveries and derive or build a model associated with that particular patient. The model can, for example derive a normal heart rate recovery by averaging the monitored heart rate recoveries over time. Other methods can, of course, be used. Over time, the patient's defined characteristic heart rate recovery will become established and the monitoring or stimulation device can then look for trends away from the established heart rate recovery.

Step 602 monitors the patient's heart rate recovery between active and less active periods. One example of an active period is an exercise period when the patient's heart rate reaches a level that is normally associated with structured exercise, such as walking, jogging, or riding a bicycle. There may be other active periods which are not necessarily associated with structured exercise, but which are desirable to observe. For example, an active period might result when the patient climbs a set of stairs in their home or office. The less active periods can typically be associated with rest periods or periods that are less active than active periods.

Figure 7:
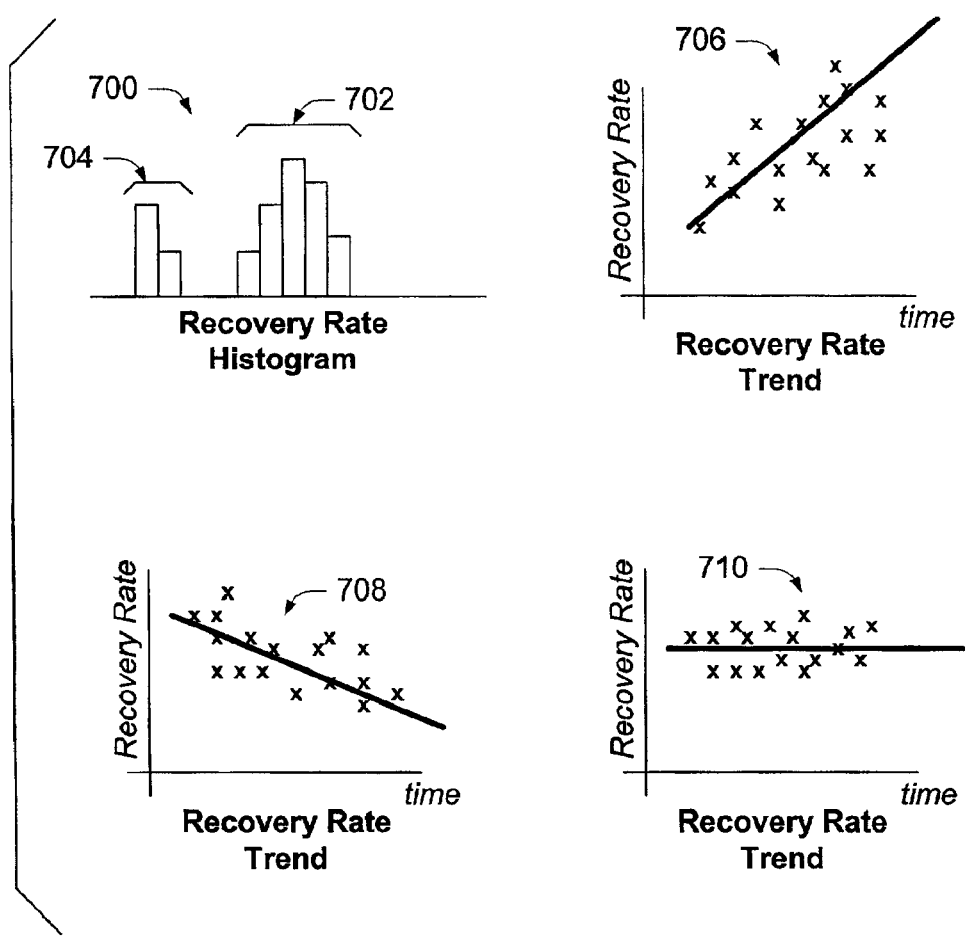
FIG. 7 illustrates exemplary ways in which heart rate recoveries can be analyzed.

Step 604 ascertains whether the monitored heart rate recovery is trending away from the defined heart rate recovery. This step can be implemented in any suitable way. As an example, consider FIG. 7. There, a couple of different methods for determining whether a patient's heart rate recovery is trending in a particular direction are shown. In one embodiment, a histogram 700 can be defined that contains bins associated with a patient's heart rate recovery. A bin collection 702 indicates what can be considered as a normal heart rate recovery for the patient. A bin collection 704 is illustrated and indicates abnormal heart rate recoveries. Thus, certain histogram bins can indicate abnormal heart rate recoveries. In another embodiment, trend graphs or trending analysis can be used to ascertain whether a patient's heart rate recovery is trending away from a normal recovery. For example, trend graph 706 indicates a number of observations "x" and a trend line superimposed over the observations. Trend graph 706 indicates that, over time, the patient's heart rate recovery is increasing. Trend graph 708, on the other hand, indicates that the patient's heart rate recovery is decreasing. Trend graph 710 indicates that the patient's heart rate recovery is not meaningfully varying. Other methods for determining heart rate recovery trends can, of course, be utilized without departing from the spirit and scope of the claimed subject matter.

If step 604 determines that the patient's heart rate recovery is not trending away from the defined heart rate recovery (or what can be considered as normal for the patient), the method returns to step 602 and continues to monitor the patient. If, on the other hand, step 604 determines that the patient's heart rate recovery is trending away from the defined heart rate recovery, then step 606 can take a remedial action.

It is to be noted that a variety of remedial actions are possible, depending on, among other things, the nature of the observed trend and the type of monitoring device being used. For example, if the observed heart rate recovery is faster than normal, the remedial actions can include pacing the patient back up to an acceptable rate if the monitoring device is a stimulation device capable of pacing a patient. If the heart rate recovery is slower than normal, then the remedial action can include notifying the physician. This can be accomplished, for example, when the patient returns to the physician's office for a routine exam. Here, the monitoring device can, in some embodiments, telemetrically provide the collected data to a suitable programmer so that the programmer can further analyze the results and/or notify the physician of the detected trend.

It should be noted and appreciated that while the above-described embodiments are directed to methods and system that consider a patient's heart rate recovery, a patient's heart rate acceleration and/or acceleration duration may provide useful metrics for assessing and treating a patient. For example, AV conduction time is also modulated by the body. Long term shifts in the AV interval versus exercise may also be markers of physiologic changes due to either disease or drugs.

CONCLUSION

By monitoring a patient's heart rate recovery using an implantable monitoring device such as an implantable stimulation device, a more complete picture of a patient's overall health can be developed. This, in turn, can permit more timely and accurate diagnoses to be rendered by physicians. In addition, having heart rate recovery information can facilitate identification of potential problems so that remedial measures or actions can be taken.

Although the invention has been described in language specific to structural features and/or methodological steps, it is to be understood that the invention defined in the appended claims is not necessarily limited to the specific features or steps described. Rather, the specific features and steps are disclosed as preferred forms of implementing the claimed invention.

What is claimed is:

1. An implantable monitoring device comprising:

one or more processors;

one or more sensors operably coupled with the one or more processors and configured to sense a patient's heart beat; and memory coupled to the one or more processors, wherein the memory stores instructions which, when executed by the one or more processors, cause the one or more processors to:

determine a patients heart rate from heart beats sensed by the one or more sensors;

detect an active period associated with a patient's physical exertion and characterized by an elevated heart rate;

detect termination of the active period as characterized by a heart rate that is slower than the elevated heart rate;

monitor the patient's heart rate recovery as the patient's heart recovers from a generally elevated rate associated with the active period, to a slower rate that is not associated with the active period; and ascertain whether the monitored heart rate recovery is normal for that patient.

2. The implantable monitoring device of claim 1, wherein the instructions cause the one or more processors to generate a notification in an event that the monitored heart rate recovery is not normal.

3. The implantable monitoring device of claim 2, wherein the instructions cause the one or more processors to effect transmission of the notification to an external device.

4. The implantable monitoring device of claim 1, wherein the instructions cause the one or more processors to save data associated with the monitored heart rate recovery on the one or more computer-readable media.

5. An implantable device comprising:

one or more processors;

one or more sensors operably coupled with the one or more processors and configured to sense a patients heart beat;

one or more activity sensors operably coupled with the one or more processors and configured to sense when a patient is active and inactive;

memory coupled to the one or more processors, wherein the memory stores instructions which, when executed by the one or more processors, cause the one or more processors to:

determine a patient's heart rate from heart beats sensed by the one or more sensors;

determine when a patient is active and inactive using the one or more activity sensors;

define a normal heart rate recovery for a patient that pertains to how the patient's heart recovers from an elevated rate associated with an active period when the patient is active, to a lower rate associated with an inactive period when the patient is less active;

monitor the patient's heart rate recovery from an active period to a less active period;

ascertain whether the monitored heart rate recovery is trending away from the normal heart rate recovery; and if the monitored heart rate recovery is trending away from the normal heart rate recovery, take a remedial action associated with remedying the monitored heart rate recovery.

6. The implantable device of claim 5, wherein the instructions cause the one or more processors to take a remedial action that determines whether stimulation therapy is desirable and, if so, administer the stimulation therapy.

7. The implantable device of claim 5, wherein the instructions cause the one or more processors to take a remedial action that generates a notification that indicates that the monitored heart rate recovery is trending away from the normal heart rate recovery.

8. An implantable device comprising:

means for monitoring a patient's heart rate;

means for ascertaining activity levels of a patient;

means for determining whether a patient's heart rate recovery between active periods and inactive periods is abnormal; and means for generating a notification that indicates the patient's heart rate recovery.

9. The implantable device of claim 8, wherein the means for generating generates a notification when the patient's heart rate recovery is abnormal.

10. The implantable device of claim 8 further comprising means for administering stimulation therapy in an event that a patients heart rate recovery is abnormal.

11. A method comprising:

detecting, with an implantable device, an active period associated with a patients physical exertion;

detecting, with the implantable device, termination of the active period;

responsive to detecting the termination, monitoring, with the implantable device, the patient's heart rate recovery as the patients heart recovers from a generally elevated rate associated with the active period, to a rate that is not associated with the active period to define a normal heart rate recovery from the elevated rate associated with the active period, to the lower rate associated with the inactive period; and saving data associated with the monitored heart rate recovery.

12. The method of claim 11 further comprising performing said acts of detecting using, at least in part, an activity sensor comprising part of the implantable device.

13. The method of claim 11 further comprising performing said acts of detecting, monitoring and saving using an implantable device comprising a stimulation device that is configured to administer stimulation therapy.

14. The method of claim 11 further comprising providing the data to an external device.

15. A method comprising:

monitoring a patient's AV interval at least during periods of exercise;

determining whether there is a shift in the patient's monitored AV interval over time; and saving data associated with the patient's monitored AV interval.

16. A method comprising:

detecting, with an implantable device, an active period associated with a patients physical exertion;

detecting, with the implantable device, termination of the active period;

responsive to detecting the termination, monitoring the patient's heart rate recovery as the patient's heart recovers from a generally elevated rate associated with the active period, to a rate that is not associated with the active period; and responsive to said monitoring, determining whether the monitored heart rate recovery is abnormal.

17. The method of claim 16 further comprising if the heart rate recovery is abnormal, determining whether the patient requires stimulation therapy and, if so, administering, with the implantable device, stimulation therapy.

18. The method of claim 16 further comprising providing data associated with the monitored heart rate recovery to an external device.

19. The method of claim 16 further comprising performing said acts of detecting using an activity sensor comprising part of the implantable device.

20. The method of claim 16 further comprising performing said acts of detecting, monitoring and determining using an implantable device comprising a stimulation device configured to administer stimulation therapy.

21. One or more computer-readable media having computer-readable instructions thereon which, when executed by one or more processors, cause the processors to implement the method of claim 16.

22. A method comprising:

defining a normal heart rate recovery for a patient that pertains to how the patients heart recovers from an elevated rate associated with an active period, to a lower rate associated with a less active period;

monitoring, with an implantable device, the patients heart during active and less active periods;

ascertaining, with the implantable device, whether the monitored heart rate recovery is trending away from the normal heart rate recovery; and if the monitored heart rate recovery is trending away from the normal heart rate recovery, taking a remedial action associated with remedying the patient's heart rate recovery.

23. The method of claim 22, wherein the act of defining comprises programming a stimulation device with the normal heart rate recovery.

24. The method of claim 22, wherein the act of defining comprises programming a stimulation device with the normal heart rate recovery by monitoring, over time, the patient's heart rate recovery and using heart rate recoveries that are monitored over time to derive a normal heart rate recovery for the patient.

25. The method of claim 22, wherein the act of taking the remedial action comprises determining, with the implantable device, whether stimulation therapy is desirable and, if so, administering stimulation therapy.

26. The method of claim 22, wherein the act of taking the remedial action comprises generating a notification that indicates an abnormal heart rate recovery.

27. One or more computer-readable media having computer-readable instructions thereon which, when executed by one or more processors, cause the processors to implement the method of claim 22.

* * * * *